US007628979B1

(12) United States Patent
Morales-Ramos et al.

(10) Patent No.: US 7,628,979 B1
(45) Date of Patent: Dec. 8, 2009

(54) USE OF CALCO OIL BLUE V IN BAIT FORMULATIONS FOR MARKING AND CONTROLLING SUBTERRANEAN TERMITES

(75) Inventors: Juan A. Morales-Ramos, Greenville, MS (US); Maria G. Rojas, Greenville, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 981 days.

(21) Appl. No.: 11/110,670

(22) Filed: Apr. 20, 2005

(51) Int. Cl.
*A01N 25/32* (2006.01)
(52) U.S. Cl. ................ 424/84; 424/410; 424/DIG. 11; 514/676; 514/596
(58) Field of Classification Search ........................ None
See application file for complete search history.

(56) References Cited

U.S. PATENT DOCUMENTS

| | | | | |
|---|---|---|---|---|
| 3,830,750 | A | * | 8/1974 | Wellman ............... 430/137.11 |
| 4,808,407 | A | * | 2/1989 | Hein et al. ................... 424/633 |
| 5,051,450 | A | * | 9/1991 | Crovetti et al. .............. 514/709 |
| 5,899,168 | A | | 5/1999 | Rojas et al. |

OTHER PUBLICATIONS

Rojas, M. Guadalupe et al., "Bait Matrix for Delivery of Chitin Synthesis Inhibitors to the Formosan Subterranean Termite (Isoptera: Rhinotermitidae)," *Journal of Economic Entomology*, Apr. 2001, vol. 94, No. 2, pp. 506-510.

Lindig, O.H. et al., "Rapid Method for Mass-Marking Boll Weevils," *Journal of Economic Entomology*, 1980, vol. 73, pp. 385-386.

Atkinson, T.H., "Use of Dyed Matrix in Bait Stations for Determining Foraging Territories of Subterranean Termites (Isoptera: Rhinotermitidae: Reticulitermes spp. and Termitidae: Amitermes Wheeleri)," *Sociobiology*, 2000, vol. 36, No. 1, pp. 149-167.

Su, Nan-Yao et al., "Evaluation of Twelve Dye Markers for Population Studies of the Eastern and Formosan Subterranean Termite (Isoptera: Rhinotermitidae)," *Sociobiology*, 1991, vol. 19, No. 2, pp. 349-362.

* cited by examiner

*Primary Examiner*—Neil Levy
(74) *Attorney, Agent, or Firm*—John D. Fado; C. Byron Stover

(57) ABSTRACT

Termite bait matrix containing cellulose, calco oil blue V (solvent blue 58 or 9,10-anthracenedione, 1,4-bis[(2-ethylhexyl)amino]), and optionally a termite toxicant (e.g., chitin synthesis inhibitor). Methods of monitoring termite activity in a region involving placing a termite bait matrix in the region and assessing the presence of termites at the site of the termite matrix, the termite bait matrix contains cellulose and 9,10-anthracenedione, 1,4-bis[(2-ethylhexyl)amino]. Methods of killing termites, involving placing a termite bait matrix in a termite habitat and allowing termites to feed on the bait matrix, the termite bait matrix contains cellulose, 9,10-anthracenedione, 1,4-bis[(2-ethylhexyl)amino], and a termite toxicant (e.g., chitin synthesis inhibitor).

15 Claims, No Drawings

USE OF CALCO OIL BLUE V IN BAIT FORMULATIONS FOR MARKING AND CONTROLLING SUBTERRANEAN TERMITES

BACKGROUND OF THE INVENTION

The present invention relates to a termite bait matrix containing cellulose, calco oil blue V (solvent blue 58 or 9,10-anthracenedione, 1,4-bis[(2-ethylhexyl)amino]), and optionally a termite toxicant (e.g., chitin synthesis inhibitor). The present invention also relates to methods of monitoring termite activity in a region involving placing a termite bait matrix in the region and assessing the presence of termites at the site of the termite matrix, the termite bait matrix contains cellulose and 9,10-anthracenedione, 1,4-bis[(2-ethylhexyl)amino]. Furthermore, the present invention relates to methods of killing termites, involving placing a termite bait matrix in a termite habitat and allowing termites to feed on the bait matrix, the termite bait matrix contains cellulose, 9,10-anthracenedione, 1,4-bis[(2-ethylhexyl)amino], and a termite toxicant (e.g., chitin synthesis inhibitor).

Damage in the United States attributable to subterranean termites is now estimated to be in excess of one billion dollars a year. All wooden or wood-containing structures are potentially affected, including homes, outbuildings, fences, utility poles, railway sleepers, boats, bridges, retaining walls, and even living trees. Since their introduction to the United States within the last half-century, Formosan subterranean termites (FST), *Coptotermes formosanus* (Shiraki), have become one of the most destructive pests in the contiguous United States. Reasons for this include their massive colonies which can contain tens of millions of individuals, their ability to attack several species of living trees, and their high level of reproduction.

The most successful existing methods for controlling subterranean termites are preventive rather than remedial. These include barrier treatments to structures and the preemptive treatment of wood materials with chemicals to prevent termite attack. These methods, however, have drawbacks. Physical barriers are not compatible for retrofitting on many existing constructions and may not be completely effective, and chemical treatments are only partially effective and last only about five years.

Low toxicity baits utilizing growth regulators have shown some success in reducing damage caused by subterranean termites, with diflubenzuron and hexaflumuron having been particularly effective in suppressing colonies of *C. formosanus* and *Reticulitermes* spp. Bait matrices utilized for the baits have consisted of cardboard, filter paper, pine wood, pure cellulose, and recently the use of a nutritionally based matrix. Depending on the species of termite, these matrices have shown to be effective toxicant carriers.

While various methodologies and compositions exist for the monitoring and control of termites, there remains a need for the creation of improved tools in this area.

SUMMARY OF THE INVENTION

In accordance with present invention there is provided a termite bait matrix containing cellulose, calco oil blue V (solvent blue 58 or 9,10-anthracenedione, 1,4-bis[(2-ethylhexyl)amino]), and optionally a termite toxicant (e.g., chitin synthesis inhibitor).

Also in accordance with the present invention there is provided a method of monitoring termite activity in a region involving placing a termite bait matrix in the region and assessing the presence of termites at the site of the termite matrix, the termite bait matrix contains cellulose and 9,10-anthracenedione, 1,4-bis[(2-ethylhexyl)amino].

Still in accordance with the present invention there is provided a method of killing termites, involving placing a termite bait matrix in a termite habitat and allowing termites to feed on the bait matrix, the termite bait matrix contains cellulose, 9,10-anthracenedione, 1,4-bis[(2-ethylhexyl)amino], and a termite toxicant (e.g., chitin synthesis inhibitor).

DETAILED DESCRIPTION OF THE INVENTION

The present invention utilizes calco oil blue V, also known as solvent blue 58 or 9,10-anthracenedione, 1,4-bis[(2-ethylhexyl)amino], within a bait formulation as a coloring agent for monitoring subterranean termites. Calco oil blue V alone in a bait formulation is non-toxic at concentrations between, for example, about 10 to about 1000 ppm; it is not a feeding deterrent to subterranean termites at concentrations between, for example, about 10 to about 500 ppm (preferably less than about 400 ppm). Calco oil blue alone in a bait formulation can be used as a marker by coloring termites that feed on the formulation since termites become visibly colored blue when feeding on matrixes containing calco oil blue V; this property makes use of calco oil blue V a good method for in-field termite marking for colony identification. This marking can be done directly in the field without the need for capturing groups of termites to force feed them the colorant in the laboratory. Current state of the art requires the collection of large numbers of termite workers for coloring in the laboratory by force feeding them filter paper with colorants; these colored termites are later released back into the original station where they were collected. This method is known as mark release recapture method of colony identification. The use of calco oil blue V in a nutritionally-based bait matrix allows marking of termites directly in the field, thus bypassing the tedious process of capturing and marking them in the laboratory for later release. The use of calco oil blue V for marking termites in the field does not allow colony size estimations, but it does allow determination of foraging areas of a given termite colony.

Calco oil blue V also acts as a synergistic compound (with, for example, chitin synthesis inhibitors such as benzoylphenyl ureas) for controlling subterranean termites. Calco oil blue V stimulates the molting process in termites. Calco oil blue V combined with a chitin synthesis inhibitor within a bait formulation accelerates the molting process which is simultaneously disrupted by the inhibition of chitin synthesis. Calco oil blue at concentrations between, for example, about 50 to about 500 ppm in combination with a chitin synthesis inhibitor reduces the time required for controlling subterranean termites and reduces the amount of toxicant required for their control. A bait formulation that contains calco oil blue V at concentrations between, for example, about 50 to about 500 ppm and a chitin synthesis inhibitor can be used to simultaneously mark and control subterranean termites, enabling the user to determine if newly detected termites have been already treated. Thus calco oil blue V can be used in baiting systems as a novel approach to reduce the amount of toxicants required to kill termites. The matrix composition may contain cellulose, water, Calco oil blue V, termite-preferred nutrients, and any of the commercially available benzoylphenyl ureas.

As noted above, calco oil blue V induces immature termites and termite workers to molt. The mechanism by which Calco oil blue V stimulates molting in termites is unknown at the present time. Without being bound by theory, one possible explanation is that this compound mimics the molecular structure of the insect molting hormone ecdysone; it is also possible that Calco oil blue V provides termites with a precursor for the synthesis of ecdysone, thereby stimulating its rapid synthesis. Calco oil blue V is not toxic to termites at the concentrations described above and it even increases survival of incipient colonies of the Formosan subterranean termites at a concentration of about 50 ppm since it possesses antimicrobial properties providing young termite colonies with protection against pathogens.

Calco oil blue V in combination with chemicals that block the synthesis of chitin has a devastating effect on termite colonies. Chitin is the basic component of an insect's exoskeleton which is completely replaced during the molting process. By stimulating molting, calco oil blue V in combination with chitin synthesis inhibitors induces an increase in defective molting and death due to the blocking of chitin synthesis. Calco oil blue V synergizes with benzoylphenyl ureas by stimulating molting and blocking chitin synthesis simultaneously, thereby inducing large number of defective molting events in a termite colony.

Calco oil blue V synergizes effectively with any commercially available benzoylphenyl ureas including, but not limited to, diflubenzuron (1-(4-chlorophenyl)-3-(2,6-difluorobenzoyl)urea), hexaflumuron (1-[3,5-dichloro-4-(1,1,2,2-tetrafluoroethoxy)phenyl]-3-(2,6-difluorobenzoyl)urea), lufenuron ((RS)-1-[2,5-dichloro-4-(1,1,2,3,3,3-hexafluoropropoxy)phenyl]-3-(2,6-difluorobenzoyl)urea), chlorfluazuron (1-[3,5-dichloro-4-(3-chloro-5-trifluoromethyl-2-pyridyloxy)phenyl]-3-(2,6-difluorobenzoyl)urea), noviflumuron ((RS)-1-[3,5-dichloro-2-fluoro-4-(1,1,2,3,3,3-hexafluoropropoxy)phenyl]-3-(2,6-difluorobenzoyl)urea), penfluron (1-(2,6-difluorobenzoyl)-3-(α,α,α-trifluoro-p-tolyl)urea), teflubenzuron (1-(3,5-dichloro-2,4-difluorophenyl)-3-(2,6-difluorobenzoyl)urea), triflumuron (1-(2-chlorobenzoyl)-3-(4-trifluoromethoxyphenyl)urea), novaluron ((RS)-1-[3-chloro-4-(1,1,2-trifluoro-2-trifluoromethoxyethoxy)phenyl]-3-(2,6-difluorobenzoyl)urea), flufenoxuron (1-[4-(2-chloro-α,α,α-trifluoro-p-tolyloxy)-2-fluorophenyl]-3-(2,6-difluorobenzoyl)urea), flucycloxuron (1-[α-(4-chloro-α-cyclopropylbenzylideneamino-oxy)-p-tolyl]-3-(2,6-difluorobenzoyl)urea), bistrifluron (1-[2-chloro-3,5-bis(trifluoromethyl)phenyl]-3-(2,6-difluorobenzoyl)urea), buprofezin (2-tert-butylimino-3-isopropyl-5-phenyl-1,3,5-thiadiazinan-4-one), and cyromazine (N-cyclopropyl-1,3,5-triazine-2,4,6-triamine). These compounds are typically applied commercially in concentrations of 1000 ppm or higher in bait formulations. However, in combination with calco oil blue V, the above compounds are surprisingly effective even at concentrations 10 times lower than their generally recommended doses to kill subterranean termites. The degree to which the presence of a particular chitin synthesis inhibitor in combination with calco oil blue V is effective in killing groups of termite workers or in eliminating termite infestations in structures may readily be assessed using methods described below and other methods known in the art.

Calco oil blue, either alone or in combination with chitin synthesis inhibitors, can be effectively delivered to the termites through the use of cellulose based bait matrixes. The cellulose may be supplied by means of any cellulose-containing material, preferably having at least 50% to greater than 95% cellulose, so long as it does not include chemicals which are repellant to termites. Such usable materials include commercially available cellulose, wood, paper, and cardboard, and are preferably in particulate form for ease of mixing with the other ingredients of the matrix. Sawdust may be used from any plant source but is preferably from woods preferred by termites such as aspen, sitka spruce, maple, birch, sweet gum and related woods or any such species possessing a low content of feeding deterrent chemicals as determinable by means well known in the art. Alternate sources of sawdust, while usable, may contain chemicals in amounts that reduce the utility of such sawdust materials due to either repellant or toxic effects. Preferably, commercially available cellulose powder is used because it is less expensive than sawdust and lacks such chemicals. The structure of calco oil blue V, also known as solvent blue 58 or 9,10 anthracenedione, 1,4-bis[(2-ethylhexyl)amino], is as follows:

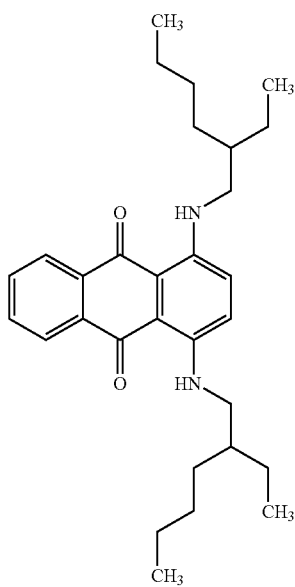

Termites prefer foods which are at least partially broken down, as by fermentation, and have pH levels produced by fermentation, i.e., less than about 5, and preferably less than about 4.5. These conditions favor the microorganisms contained in termite guts, including protozoans and bacteria, which break down and digest cellulose. The termite body surface also carries fungal spores which in nature infect the food material and, after a period of time in which fungal growth is established, render it more nutritious. Thus fresh wood material is not a preferred termite food. The termite matrices of this invention possess both appropriate pH and odors indicative of ongoing fermentation processes, both of which serve to attract termites.

The termite matrices of this invention therefore preferably comprise feed-conditioning substances (or breakdown products thereof) which cause the matrices to simulate natural termite foods having a degree of fermentation (infestation with microorganisms and their products), which is attractive to termites. Through use of such conditioning agents, the matrices emit smells attractive to termites. Such conditioning agents include pH-adjusting agents such as hydrochloric, acetic or other acids which are not toxic to termites in the amounts used, present in quantities sufficient to lower the pH of the food to 5 or less. Ethyl alcohol is also used for its ability to dissolve fats and sterols and attract termites. The ethyl alcohol is used in amounts sufficient for its effects to be detected by termites but at a level that does not interfere with the growth of essential microorganisms in the matrix, with this being in an amount ranging from about 0 to about 8 ml/kg of matrix. Preferably, ethyl alcohol is used in amounts between about 0.5 and about 8 ml/kg of matrix. As will be understood by those skilled in the art, if the matrix is heat-sterilized prior to use, the volatile alcohol will evaporate; however, the matrix will contain products resulting from action of the alcohol on other components. Yeast hydrolysate is also a preferred conditioning substance.

If no feed-conditioning substances are used, a period of two or three weeks, depending on the ambient temperature, should be allowed for fermentation to occur to make the matrix attractive to termites.

The degree to which the presence of a particular component causes termites to prefer a food over other foods not containing the component, or containing greater or lesser amounts thereof, may readily be assessed using methods known in the art.

The matrix also may comprise vitamins and amino acids characteristic of naturally-occurring termite food or attractive to termites, including vitamins such as riboflavin, D-biotin, choline chloride, vitamin B-12, folic acid, myo-inositol, nicotinamide, calcium pantothenate, pyridoxal hydrochloride, thiamine and ascorbic acid; and amino acids such as L-glutamic acid, L-histidine, L-glutamine, L-alanine, L-lysine, L-isoluecine, L-proline, and L-tyrosine. Vitamin and amino acid-containing materials include yeast and yeast hydrolysate, as well as synthetic solutions that contain these chemicals. Yeast hydrolysate is preferred because of its ability to also act as a food conditioning agent. The vitamins and amino acids may be present in the food at aggregate ratios sufficient to be detectable by termites up to amounts which cause these insects to stop feeding. In the case of yeast hydrolysate, preferred amounts are between about 0.1 g/kg and about 3 g/kg of matrix, more preferably from about 1.0 g/kg of matrix to about 2.0 g/kg of matrix, and most preferably about 1.5 g/kg of matrix. Although it is not necessary that any particular vitamin or amino acid be present in detectable amounts, the aggregate amount of vitamins and amino acids should be present in amounts sufficient to cause the termites to exhibit a preference for foods containing these substances over their ordinary wood diet.

The termite matrix of this invention preferably contains a lipid, preferably a fat or phospholipid which is a source of choline chloride and fatty acids such as linolenic, palmitic, palmetoleic and oleic acids, which are most preferably found in lecithin. Vegetable oils such as canola oil, corn oil, soybean oil, cotton oil, and other oils known to the art may also be used, as these contain desirably fatty acids such as linolenic acid. If oils such as these not containing choline chloride are used, choline chloride may be added separately to the matrix. The concentration of lipid in the matrix is sufficient to be detectable by termites and less than that causing termite refusal of the food. In the case of lecithin, this amount ranges from about 0.1 g/kg of food to about 12.5 g/kg of matrix, preferably from about 1 g/kg of matrix to about 2 g/kg of matrix, and is most preferably about 1.25 g/kg of matrix.

The matrix may comprise a growth factor required for termite growth, reproduction, and/or chitin formation. Preferably, the growth factor is ergosterol, a sterol produced by fungal infection of food materials by spores carried on the termite body, which emits a characteristic smell attractive to termites. Other useful growth factors include fatty acids and amino acids, such as the nutrients described above, and preferably linolenic acid. The growth factor should be present in an amount sufficient to be detectable by termites, but not so great as to be toxic or cause termites to refuse to feed on the matrix. In the case of ergosterol, the ratio of ergosterol to food is preferably between about 0 and about 4.5 g/kg of matrix, more preferably from about 0.2 g/kg of matrix to about 1.0 g/kg of matrix, and most preferably is about 0.45 g/kg of matrix.

The matrix may further comprise salts useful to termites such as calcium chloride, cobalt chloride, ferric chloride, zinc chloride, potassium phosphate, sodium phosphate, magnesium sulfate, copper sulfate, and manganese sulfate. Amounts of salts may vary. Salts are preferably present in the food in amounts sufficient to that the aggregate ratio of salts to matrix is sufficient to cause the termites to exhibit a preference for the matrix. A good source of such salts is commercially available bottled drinking or spring water, preferably below a pH of about 6, which can be used to provide the requisite moisture for the matrix. Barbe's™ water, available from Barbe's Dairy Company, West Wego, La., is a preferred water to supply salts to the matrix.

The matrix further comprises Calco oil blue V or C.I. solvent blue 58 (blue) (9,10-anthracenedione, 1,4-bis[(2-ethylhexyl)amino]-$C_{30}H_{42}N_2O_2$, CAS No. 29887-08-9) present in amounts ranging from about 10 ppm to about 1000 ppm.

Subterranean termites prefer moist foods. To be more attractive than other available foods in the environment, the formulation of this invention should be preferably moist. Enough water should be used to allow mixing of the matrix material, and/or completely hydrate the particulate or solid cellulose materials and to provide excess water to maintain a humid environment. In general about three-fourths by weight of the matrix should be water, but this may vary with the water content ranging from about 20% to about 90% by weight of the composition.

A water-retention agent capable of absorbing water and releasing it slowly to the environment can be used to ensure an acceptable moisture level in the matrix material as well as to serve as another means for termite aggregation. Examples of such materials include agar and polyacrylamide, but may include any substance not otherwise possessing a repellant effect. Examples of preferred usable materials include the polyacrylamide graft copolymer such as TERRAWET T-400 Aquawet (Terrawet Company, San Diego, Calif.), which can absorb and retain up to a thousand times their own weight in water. These materials should be hydrated, preferably fully-hydrated, with the addition of at least thirty times their weight in water containing the Calco oil blue. The hydrated water-retaining materials may be mixed with the matrix.

Termites are attracted during their foraging to high humidity conditions, preferably at least about 80% humidity, and more preferably at least about 90% humidity. Thus, moisture-retaining material as described above is preferably placed in the immediate environment of the bait matrix to provide a humidity readily detectable by, and attractive to, termites. In a preferred embodiment in which a polyacrylamide graft copolymer such as TERRAWET 400 Aquawet is used as the water-retaining agent, it may be placed in the area of a termite bait or monitoring station at an application rate effective for eliciting an aggregant response, that is, from about 1 g to about 10 g (dry weight) per square foot. The hydrated-polyacrylamide, preferably hydrated to a Calco oil blue: polymer weight ratio of at least about 30:1, with a final concentration of Calco oil blue of 900 ppm, can be injected into the soil around the bait station by pressure using commercially available injectors, preferably to a radius around the bait matrix of at least about 2.5 cm, or placing it on the base of the station or inside of the above ground station or in the cracks of walls and trees or other locations susceptible to termite infestation. Other water-retaining agents as described above can alternatively be used, adjusting ratios to achieve 80% to 90% humidity as will be readily apparent to those skilled in the art. The bait container is made from a material such as paraffin, beeswax, polyurethane foam, styrofoam and fibrous casing tubes.

The termite matrix of this invention may be used to attract termites to its immediate environment for purposes of monitoring the size and presence of termite populations, e.g., by observing termites and counting or otherwise estimating the number of termites present by measuring the consumption of matrix. Typical monitoring strategies utilize approximately one bait station per 10-15 linear feet. The significantly faster response of termites to the bait matrix of this invention compared to the pine wood conventionally used results in enhanced monitoring efficacy, and means that shorter periods between inspections may be required than is the case with pine wood. Additionally, the bait matrix of this invention may be used in combination with a preferred wood or yellow pine wood to extend the period of termite activity at the monitoring site.

The termite matrix of this invention may also be used as a carrier for any conventional termite toxicant such as hexaflumuron, imidacloprid and 5-amino-1-[2,6-dichloro-4-(trifluoromethyl)phenyl]-4-[(3-fluoromethyl)-sulfonyl]-1-H-pyrazole-3-carbonitride (referred to herein as "fipronil") of Chem Service, Inc., West Chester, Pa. Other bioactive compounds not conventionally recognized as termite toxicants may also be used as termiticides. These include streptomycin sulfate, rifampicin, albendazole, neomycin sulfate, sorbic acid, and commercially available antimycotics such as antibiotic antimycotic available from Sigma Company, St. Louis, Mo. For biocidal efficacy, toxins must be present in amounts less than those detectable by termites, with this amount typically being less than about 1000 ppm for hexaflumuron, imidacloprid, and fipronil and other antimicrobials. Due to the high rate of consumption induced by the feed matrix of the instant invention, satisfactory kill of termites can be achieved with toxicant concentrations well below the rejection threshold. Useful amounts typically range from about 1 ppm to about 200 ppm of the bait composition. Preferred concentrations, while being readily determinable by conventional methods, are typically about 25 to about 50 ppm for hexaflumuron, about 1 to about 5 ppm for imidacloprid and fipronil, and about 5 to about 12.5 ppm for other antimicrobials.

The matrix materials of this invention, with or without toxins, may be encased in materials or containers which are water-retentive such that they substantially prevent evaporation of the moisture in the food, but which are vapor-permeable to a degree sufficient to allow termites to detect odors coming from the matrix. Suitable materials may be readily determined by the practicing artisan and include hard waxes with low melting points such as paraffin or beeswax in which pieces of the matrix material can be dipped or which can be otherwise coated on the matrix, and moldable polymers such as styrofoam, and polyurethane foams such as GREAT STUFF, Flexible Products Company, Joliet, Ill. Fibrous casing tubes for sausages such as those available from L.E.M. Products, Inc., Miamitown, Ohio, which consists of cotton fibers coated with wax, turned inside out so as not to present the wax surface to the termites, are also preferred materials to be used for containers for the matrices of this invention.

Unless defined otherwise, all technical and scientific terms used herein have the same meaning as commonly understood by one of ordinary skill in the art to which the invention belongs. Although any methods and materials similar to equivalent to those described herein can be used in the practice or testing of the present invention, the preferred methods and materials are now described.

The following examples are intended only to further illustrate the invention and are not intended to limit the scope of the invention as defined by the claims.

EXAMPLES

Example 1

Matrix Preparation:

(1) Calco Oil Blue Solution. From 50-1000 g of calco oil blue V or C.I. solvent blue 58 (blue) (9,10-anthracenedione, 1,4-bis[(2-ethylhexul)amino]-$C_{30}H_{42}N_2O_2$ (Product number 62418, CAS No 29887-08-9, Pylam Products Co. Inc., Tempe, Ariz.)) were individually mixed with 0.500 ml canola oil (Hunt-Wesson, Inc., Fullerton, Calif.) in a 800 ml glass beaker, and then 150 ml of 200 proof dehydrated alcohol, U.S.P. punctilious (Product No. #194A31, Quantum Chemical Co., Tuscola, Ill.) and 150 ml acetone (T.J. Baker #9010-03) were sequentially added and the solution was thoroughly homogenized.

(2) Mixing with Cellulose Powder. The calco oil blue V solution (of each concentration) was then mixed with 333 g powdered alpha cellulose fiber (Product number 3425, Bioserv Co., Frenchtown, N.J.) contained in a 4 L stainless steel bowl. Calco oil blue V residues in the beaker were rinsed twice with equal amounts of the ethanol (75 ml each) and decanted onto the colored alpha cellulose mixture. The mixture was homogenized using a large stainless steel spoon and placed under a hood at room temperature until all the solvent evaporated. The dry colored alpha cellulose was placed into individual plastic containers, tightly closed and stored at room temperature.

(3) Incorporation of Nutrients. The dry colored alpha cellulose was then mixed with the nutritive liquid (described in U.S. Pat. No. 6,585,991 which is incorporated by reference in its entirety). The nutritive liquid was prepared by weighing 1.25 g lecithin (USB #18240), 0.450 g ergosterol (Sigma #E-6510), 3.75 g ethyl alcohol (Quantum MT #194A31), and 650 g drinking water (Barbe's dairy, West Wego, La.) into a 1 L glass bottle and mixing well using a glass bar. The opening of the bottle was covered with a foam stopper, the bottle cap was loosely placed on top of the stopper, and the stopper covered with foil. After autoclaving for 20 min at 120° C., the bottle was closed tightly and allowed to cool down. Under a laminar flow hood, yeast hydrolysate (ICN Biomed. #103304) was added to the lecithin-containing mixture using a sterile spatula and the mixture was shaken until the yeast hydrolysate was incorporated. The bottle was tightly closed. Using a sterile spatula, 667 ml lecithin-yeast hydrolysate-containing mixture was added to 333 g colored cellulose (at each of the calco oil blue V concentrations) and mixed well. The beaker was covered with foil and plastic to avoid contamination and loss of water. This mixture was stored at 5° C. up to 8 months or at room temperature for at least a month. The mixture was compacted and divided into pieces of about 25-50 g each at colorant concentrations of 50, 100, 225, 250, 500, and 750 ppm respectively. Chitin synthesis inhibitors such as Diflubenzuron (Ensystex) at a given concentration of 50, 100, 175, 200, and 250 ppm were individually weighed, dissolved in minimal amount of acetone (J. T. Baker #9010-

03) in a 50 ml plastic tube, and added to the sterile liquid solution. Preliminary results testing a dose range of 50, 100, 225, 250, and 750 ppm had shown that 225 ppm of the blue colorant in combination with a chitin synthesis inhibitor (50-175 ppm, respectively) was sufficient to induce FS termite mortality within approximately 2 months without any signs of repellence to the termites. Some repellence was observed at colorant doses higher than 500 ppm.

A concentration of 225 ppm Calco oil blue was effective as bait active ingredient taking a mean time to kill *C. formosanus* of 2.0 months under laboratory conditions. Concentrations greater than 500 and up to 1000 ppm were also effective, but bait consumption was reduced and mean killing times were not significantly different.

Example 2

(Colorant: CSI Dose Determination):

Under a laminar flow hood, 66 g colored cellulose powder at concentration of 50, 100, 225, 250, 500, or 750 ppm (0.010, 0.020, 0.045, 0.050, 0.100, or 0.150 g, respectively) from example 1 was mixed with 135 ml of sterile nutritional supplement (formulated as in example 1) in a 250 ml sterile glass beaker (prepared as reported by Rojas, M. G. and Morales-Ramos, J. A., "Bait matrix for delivery of chitin synthesis inhibitors to the Formosan subterranean termite [Isoptera: Rhinotermitidae]," J. Econ. Entomol., 94(2): 506-510 (2001)). A dose of 175 ppm of diflubenzuron was added to the formulations containing 50 and 100 ppm of calco oil blue. A lower dose of 50 ppm of diflubenzuron was added to the formulations containing 225 and 500 ppm of calco oil blue. The mixture was manually homogenized using a stainless steel spatula. To encase the bait matrix, tubes made of fibrous casing material (#124B; L.E.M. Products, Inc., Miamitown, Ohio) were cut into 150 mm long portions as reported by Rojas and Morales-Ramos (2001) supra. Fifty grams of bait matrix containing the blue colorant was compacted into one end of the inlet tube, at which point the open end of the inlet tube was closed with a rubber band. The bait casing was placed inside the foraging box adjacent to a 10 g piece of pine wood, taking care that they were partially covered with the sand. Control bait matrix was prepared minus blue colorant, and presented in the same was as the treatment matrix to Formosan subterranean termite workers taken from four different colonies, with 3 boxes per locality totaling twelve boxes of 1000 termites per treatment (Rojas and Morales-Ramos supra). All the experimental boxes were maintained under darkness at 27±1° C. and 90±2% relative humidity. Observations were done every 72 hours until all the termites died. The time to reach 100% mortality was measured and recorded. Mean comparisons among treatments and control were conducted.

The experimental colony, after exposure to the formulation containing calco oil blue V and diflubenzuron, were dead in about two months and a half while the control boxes were still alive after 3 months (Table 1). The cuticle of the dead termites from the treatment boxes had a blue color as well as their tunnels and surrounding sand. After a month of the termites being exposed to the formulation containing 225 ppm of calco blue and 50 ppm of diflubenzuron, and a month and a half to the formulations containing 50 ppm or 100 ppm of calco blue and 175 ppm of diflubenzuron, immature termites molted prematurely. This resulted in workers and soldiers with malformed mandibles, and nymphs (pre-reproductives) with soldier shaped heads, cuticle partially hardened and partial adult coloration with wrinkled and reduced wings. At concentration of blue>225 ppm, the acceptability of the bait was reduced since some termite colonies required more than 8 hrs to begin feeding on the formulations. This chemical combination acted against the termites, producing a mortality of a 1000-worker colony in about 4 weeks, depending on the health and age of the colony. At calco blue concentrations above 750 ppm, the bait becomes unpalatable and consumption is almost nonexistent at concentrations above 1000 ppm. The preferred dose is 225 mg of Calco oil blue V per kilogram of bait matrix and 50 ppm of a chitin synthesis inhibitor.

TABLE 1

Groups of 1000 termite workers alive after 1 and 2 months of feeding on non-repellent lethal concentrations of Calco oil blue V.

| Calco Oil blue V[a] | Diflubenzuron[a] | 1 Month Alive | 2 Months Alive | 3 Months Alive |
|---|---|---|---|---|
| 0 (Control) | 0 | 12 | 12 | 12 |
| 50 | 175 | 11 | 10 | 5 |
| 100 | 175 | 9 | 4 | 1 |
| 225 | 50 | 7 | 2 | 0 |
| 500 | 50 | 9 | 4 | 3 |

[a]Concentration in parts per million.

Example 3

(In-Field Marking and Control):

Formosan subterranean termite and native subterranean termite infested trees (Water Oaks and Legastrums) in New Orleans, La. were chosen for this study. Three sites were selected located at the Southern Regional Research Center campus. Site 1 was located near the service building next to an old water oak tree, site 2 was located in the compound area near ligastrum trees, and site 3 near ligastrum trees outside the compound area. Sites 1 and 2 were active with Formosan subterranean termites and site 3 with Eastern subterranean termites.

The colored bait matrix at 250 ppm was encapsulated as described above and placed directly in the base of the trees where termites were foraging, making sure that the encapsulated colored bait matrix was covered with soil or with a piece of wood or brick on top of it to prevent desiccation. The bait was periodically inspected for consumption and termite activity. The field study started in early August and was completed by the end of the following June. During winter (December-February) termite activity decreased considerably, but by April termite activity and foraging resumed and the blue colored matrix was replaced by bait formulation containing 250 ppm of chitin synthesis inhibitors to kill the colonies. Diflubenzuron was used in 2 of the sites and chlorfluazuron was used in the remaining site.

Termites were visibly colored blue after feeding the colored bait matrix that did not contain diflubenzuron. Matrix with calco oil blue V alone did not kill the termite colonies nor reduce termite activity. Termite workers remained visibly colored 1 week after removing the blue colored bait formulation. When the bait formulation containing chitin synthesis inhibitors was added 3 months later, termite activity was high showing that calco oil blue did not have an affect on the termite colonies. The calco oil blue colorant, however, surprisingly acted as a synergist, requiring minimal amount of chitin synthesis inhibitors to eliminate the colonies in a period of only 2 months. Termites have not been subsequently detected in the treated areas.

TABLE 2

Bait consumption (g) by subterranean termites in a field test on USDA-ARS-SRRC campus, New Orleans, LA

| | Site 1 (Water Oak) | | Site 2 (Ligastrum) | | Site 3 (Ligastrum) | |
|---|---|---|---|---|---|---|
| Days | Calco Blue | Diflubenzuron | Calco Blue | Chlorfluazuron | Calco Blue | Diflubenzuron |
| 7 | 0 | 0 | 0 | 0 | 0 | 0 |
| 14 | 150 | 0 | 200 | 0 | 200 | 0 |
| 21 | 350 | 0 | 450 | 0 | 150 | 0 |
| 27 | 400 | 0 | 300 | 0 | 150 | 0 |
| 46 | 400 | 0 | 250 | 0 | 100 | 0 |
| 56 | 100 | 0 | 350 | 0 | 0 | 0 |
| 73 | 0 | 0 | 250 | 0 | 0 | 0 |
| 83 | 0 | 0 | 300 | 0 | 0 | 0 |
| 102 | 0 | 0 | 400 | 0 | 0 | 0 |
| 159 | 0 | 0 | 200 | 0 | 0 | 0 |
| 221 | 0 | 0 | 0 | 0 | 0 | 0 |
| 251 | 0 | 150 | 0 | 450 | 0 | 150 |
| 281 | 0 | 300 | 0 | 750 | 0 | 300 |

Bait consumption calculated from fully consumed bait bags

All of the references cited herein are incorporated by reference in their entirety. Also incorporated by reference in their entirety is the following reference: Lindig, O. H., et al., J. Econ. Entomol. 73: 385-386 (1980). Also incorporated by reference in their entirety are the following U.S. Pat. Nos. 6,824,787; 6,691,453; 6,585,991.

Thus, in view of the above, the present invention concerns (in part) the following:

A termite bait matrix comprising (or consisting essentially of or consisting of) cellulose, 9,10-anthracenedione, 1,4-bis[(2-ethylhexyl)amino], and optionally a termite toxicant.

The above termite bait matrix, wherein said matrix contains about 10 to about 1000 ppm, 9,10-anthracenedione, 1,4-bis[(2-ethylhexyl)amino] or about 50 to about 750 ppm or about 50 to about 500 ppm or about 100 to about 400 ppm or about 200 to about 400 ppm 9,10-anthracenedione, 1,4-bis[(2-ethylhexyl)amino].

The above termite bait matrix, wherein said matrix contains a termite toxicant.

The above termite bait matrix, wherein said termite toxicant is a chitin synthesis inhibitor.

The above termite bait matrix, wherein said matrix contains about 10 to about 1000 ppm of said chitin synthesis inhibitor or about 50 to about 500 ppm or about 50 to about 250 ppm of said chitin synthesis inhibitor or about 50 to about 100 ppm of said chitin synthesis inhibitor.

The above termite bait matrix, wherein said chitin synthesis inhibitor is a benzoylphenyl urea.

The above termite bait matrix, wherein said matrix further comprises water; a lipid preferred by termites, wherein said lipid is a source of choline chloride, fatty acids, or both; and one or more termite-preferred nutrients in amounts sufficient that said termite matrix is preferred by termites over wood; and a feed conditioning substance or breakdown product thereof effective for simulating fermented termite foods and which is attractive to termites.

The above termite bait matrix, wherein said lipid is selected from the group consisting of lecithin and vegetable oils.

The above termite bait matrix, wherein said termite-preferred nutrients are selected from the group consisting of vitamins and amino acids.

The above termite bait matrix, wherein said termite-preferred nutrients are in the form of yeast or yeast hydrolsyate.

The above termite bait matrix, wherein said feed conditioning substance or breakdown product thereof is selected from the group consisting of pH adjusting agents, ethyl alcohol, yeast hydrolysate, and combinations thereof.

The above termite bait matrix, wherein said cellulose is selected from the group consisting of sawdust and cellulose powder.

The above termite bait matrix, wherein said matrix further comprises lecithin in an amount between about 0.1 and about 12.5 g/kg of said matrix, ergosterol in an amount ranging from about 0 to about 4.5 g/kg of said matrix, yeast hydrolysate in an amount between about 0.1 and about 3 g/kg of said matrix, ethyl alcohol in an amount ranging from about 0 to about 8 ml/kg of said matrix, cellulose in an amount of about 250 g/kg of said matrix; and water.

The above termite bait matrix, further comprising water (e.g., in an amount between about 50 to 90% of said matrix, by weight); a lipid preferred by termites, wherein said lipid is a source of choline chloride, fatty acids, or both; and one or more termite-preferred nutrients in amounts sufficient that said termite matrix is preferred by termites over wood; for example the lipid may be lecithin and/or vegetable oils; for example the termite-preferred nutrients may be vitamins and/or amino acids or yeast and/or yeast hydrolsyate.

The above termite bait matrix, further comprising a water-retention agent (e.g., in an amount between about 0 and about 0.05 g/kg of said matrix); for example agar and/or polyacrylamide.

The above termite bait matrix wherein said termite bait matrix is contained within a water-retentive, vapor-permeable coating or container.

The above termite bait matrix wherein said termite bait matrix has a pH less than about 5.

The above termite bait matrix wherein said termite bait matrix further comprises a feed conditioning substance or breakdown product thereof effective for simulating fermented termite foods and which is attractive to termites; for example pH adjusting agents, ethyl alcohol, yeast hydrolysate, and combinations thereof.

The above termite bait matrix further comprising one or more termite growth factors (e.g., ergosterol and/or linolenic acid).

The above termite bait matrix further comprising a water-retentive, vapor-permeable barrier.

The above termite bait matrix wherein said termite bait matrix is contained within a termite-accessible container or coating.

The above termite bait matrix further comprising one or more naphthalenic compounds (e.g., N-hydroxynaphthalimide and sodium, magnesium, potassium and calcium salts thereof, 1,8-napthalimide, copper naphthenate and zinc naphthenate, and mixtures thereof) in amounts sufficient in termite matrices to kill termites.

The above termite bait matrix further comprising a termite toxicant (e.g., streptomycin sulfate, rifampicin, albendazole, neomycin sulfate, sorbic acid, antimycotics, benzofenyl ureas, imidacloprid, hydroximethanon, juvenile hormone mimics, and mixtures thereof).

The above termite bait matrix further comprising a nitrogen containing compound (e.g., urea and/or uric acid) in an amount effective to stimulate termites to feed or mask the unattractiveness of other compounds or both, and wherein the total concentration of said nitrogen containing compound plus any endogenous amino acids, polypeptides, and proteins in said bait matrix is between about 10 to about 1000 ppm or between about 100 to 500 ppm, and further wherein said nitrogen containing compound is not present in a termiticidally effective amount.

A method of monitoring termite activity in a region, said method comprising placing a termite bait matrix according to claim 1 in said region and assessing the presence of termites at the site of said termite matrix. Wherein said matrix does not contain a termite toxicant.

A method of killing termites, said method comprising placing a termite bait matrix according to claim 1 in a termite habitat and allowing termites to feed on said bait matrix, wherein said matrix contains a termite toxicant.

The above method, wherein said termite toxicant is a chitin synthesis inhibitor.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A termite bait matrix consisting essentially of cellulose, 9,10-anthracenedione, 1,4-bis[(2-ethylhexyl)amino], and a termite toxicant, wherein said matrix contains 50 to 250 ppm 9,10-anthracenedione, 1,4-bis[(2-ethylhexyl)amino] and said termite toxicant is a chitin synthesis inhibitor.

2. The termite bait matrix according to claim 1, wherein said cellulose is selected from the group consisting of sawdust and cellulose powder.

3. The termite bait matrix according to claim 1, wherein said matrix further comprises water; a lipid preferred by termites, wherein said lipid is a source of choline chloride, fatty acids, or both; and one or more termite-preferred nutrients in amounts sufficient that said termite matrix is preferred by termites over wood; and a feed conditioning substance or breakdown product thereof effective for simulating fermented termite foods and which is attractive to termites.

4. The termite bait matrix according to claim 3, wherein said lipid is selected from the group consisting of lecithin and vegetable oils.

5. The termite bait matrix according to claim 3, wherein said feed conditioning substance or breakdown product thereof is selected from the group consisting of pH adjusting agents, ethyl alcohol, yeast hydrolysate, and combinations thereof.

6. The termite bait matrix according to claim 3, wherein said termite-preferred nutrients are selected from the group consisting of vitamins and amino acids.

7. The termite bait matrix according to claim 6, wherein said termite-preferred nutrients are in the form of yeast or yeast hydrolysate.

8. The termite bait matrix according to claim 1, wherein said chitin synthesis inhibitor is a benzoylphenyl urea.

9. The termite bait matrix according to claim 1, wherein said matrix contains about 10 to about 1000 ppm of said chitin synthesis inhibitor.

10. The termite bait matrix according to claim 1, wherein said matrix contains about 50 to about 500 ppm of said chitin synthesis inhibitor.

11. The termite bait matrix according to claim 1, wherein said matrix contains about 50 to about 250 ppm of said chitin synthesis inhibitor.

12. The termite bait matrix according to claim 1, wherein said matrix contains about 50 to about 100 ppm of said chitin synthesis inhibitor.

13. The termite bait matrix according to claim 1, wherein said matrix further comprises lecithin in an amount between about 0.1 and about 12.5 g/kg of said matrix, ergosterol in an amount ranging from about 0 to about 4.5 g/kg of said matrix, yeast hydrolysate in an amount between about 0.1 and about 3 g/kg of said matrix, ethyl alcohol in an amount ranging from about 0 to about 8 ml/kg of said matrix, cellulose in an amount of about 250 g/kg of said matrix; and water.

14. The termite bait matrix according to claim 1, wherein said termite bait matrix consists of cellulose, 9,10-anthracenedione, 1,4-bis[(2-ethylhexyl)amino], and a termite toxicant, wherein said matrix contains 50 to 250 ppm 9,10-anthracenedione, 1,4-bis[(2-ethylhexyl)amino] and said termite toxicant is a chitin synthesis inhibitor; and optionally water, a lipid preferred by termites wherein said lipid is a source of choline chloride, fatty acids, or both, and one or more termite-preferred nutrients in amounts sufficient that said termite matrix is preferred by termites over wood, and a feed conditioning substance or breakdown product thereof effective for simulating fermented termite foods and which is attractive to termites; and optionally lecithin in an amount between about 0.1 and about 12.5 g/kg of said matrix, ergosterol in an amount ranging from about 0 to about 4.5 g/kg of said matrix, yeast hydrolysate in an amount between about 0.1 and about 3 g/kg of said matrix, ethyl alcohol in an amount ranging from about 0 to about 8 ml/kg of said matrix, cellulose in an amount of about 250 g/kg of said matrix, and water.

15. A method of killing termites, said method comprising placing a termite bait matrix according to claim 1 in a termite habitat and allowing termites to feed on said bait matrix, wherein said matrix contains a termite toxicant.

* * * * *